United States Patent
Zhang et al.

(10) Patent No.: US 7,471,970 B2
(45) Date of Patent: Dec. 30, 2008

(54) METHOD FOR MEASURING BLOOD OXYGEN CONTENT UNDER LOW PERFUSION

(75) Inventors: Xu Zhang, Nanshan (CN); Jilun Ye, Nanshan (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 481 days.

(21) Appl. No.: 11/316,060

(22) Filed: Dec. 22, 2005

(65) Prior Publication Data

US 2006/0206019 A1    Sep. 14, 2006

(30) Foreign Application Priority Data

Mar. 10, 2005   (CN) ..................... 2005 1 0033594

(51) Int. Cl.
*A61B 5/1455* (2006.01)

(52) U.S. Cl. ........................ 600/323; 600/322

(58) Field of Classification Search ................. 600/322, 600/323; 356/39, 41
See application file for complete search history.

(56) References Cited

U.S. PATENT DOCUMENTS

| | | | | |
|---|---|---|---|---|
| 4,807,631 | A | * | 2/1989 | Hersh et al. .................. 600/323 |
| 5,485,847 | A | * | 1/1996 | Baker, Jr. .................... 600/323 |
| 5,853,364 | A | * | 12/1998 | Baker et al. .................. 600/300 |
| 6,094,592 | A | | 7/2000 | Yorkey et al. |
| 6,151,107 | A | | 11/2000 | Schollermann et al. |
| 6,157,850 | A | | 12/2000 | Diab et al. |
| 6,334,065 | B1 | * | 12/2001 | Al-Ali et al. ................ 600/323 |
| 2003/0036689 | A1 | * | 2/2003 | Diab et al. ................... 600/323 |
| 2004/0044276 | A1 | * | 3/2004 | Arnold ....................... 600/323 |

FOREIGN PATENT DOCUMENTS

| | | |
|---|---|---|
| CN | 1148794 | 4/1997 |
| JP | 2003-153882 | 5/2003 |
| JP | 2004-202190 | 7/2004 |

* cited by examiner

*Primary Examiner*—Eric F Winakur
*Assistant Examiner*—Etsub D Berhanu
(74) *Attorney, Agent, or Firm*—Kory D. Christensen; Stoel Rives LLP

(57) ABSTRACT

A method for measuring blood oxygen content under low perfusion, which is used in a device for measuring blood oxygen content, includes the steps of: initializing the device that is applied with power, collecting and processing data with a driving circuit of light emitting device, a bias circuit, a gain circuit and an A/D sampling circuit, which are controlled under a core control module; calculating blood oxygen saturation based on the collected data with a data processing module which integrates the collected data in a period of time with an area integration method; and outputting from a communication functional module results of the blood oxygen saturation or pulse rate calculated with the data processing module. The method further includes a decision step of deciding the two results acquired from the data processing module with the waveform method and the integration method respectively based on the intensity of the measured signal and generating the final measured result, performed by a decision unit included in the device. By adopting the above method, the disturbance to effective signal by noise can be eliminated. As a result, the measuring accuracy of blood oxygen content under low perfusion can be improved without increasing the production cost for the measuring device.

18 Claims, 5 Drawing Sheets

METHOD FOR MEASURING BLOOD OXYGEN CONTENT UNDER LOW PERFUSION

FIELD OF THE INVENTION

The present invention relates to medical instruments, more particularly to a device for measuring blood oxygen saturation, and especially to a method for measuring blood oxygen content under low perfusion.

BACKGROUNGD OF THE INVENTION

It is very necessary to monitor the state of blood oxygen for patients in the process of operation and reablement, generally, by monitoring a parameter of blood oxygen saturation. Conventionally, the above parameter is measured with spectrophotometry which utilizes the difference between light absorption coefficients of reduced hemoglobin and oxyhemoglobin based on the Lambert-Beer law and the theory of light scattering. The spectrophotomety can be performed by transmitted light or reflected light. The Lambert-Beer law is expressed as:

$$I = I_0 e^{-\epsilon cd},$$

Where I is the intensity of transmitted light, $I_0$ is the intensity of incident light, C is the concentration of the light-receiving matter in solution, d is the path length of light absorbed by solution, and $\epsilon$ is the light absorption coefficient of the matter. From the above equation, the absorbance D is reached as follows:

$$D = \ln I_0/I = \epsilon cd.$$

It indicates that the light absorption of the matter correlates with the concentration thereof, which implies the possibility of calculating internal composition of tissues from the light absorption of them.

The researchers have further researched the reduced hemoglobin (Hb) and the oxyhemoglobin ($HbO_2$) closely correlating with the blood oxygen saturation. It is found that the difference between the light absorption coefficients of $HbO_2$ and Hb is notable, as shown in FIG. 2, in which the solid line represents the light absorption coefficient-wavelength curve of $HbO_2$, and the dotted line represents the light absorption coefficient-wavelength curve of Hb. It is shown in FIG. 2 that the light absorption coefficient of $HbO_2$ is only one tenth (1/10) of that of Hb for the visible red light with wavelength of 660 nm, but the light absorption coefficient of $HbO_2$ is greater than that of Hb for the infrared light with wavelength of 940 nm, and the light absorption coefficients of $HbO_2$ and Hb have one isoabsorption point for the infrared light with wavelength of 805 nm.

The arterial blood oxygen saturation is defined as:

$$SaO_2 = HbO_2/(Hb+HbO_2) = C_1/(C_1+C_2), \quad (1)$$

where $C_1$ is the concentration of $HbO_2$, and $C_2$ is the concentration of Hb. Since $$D(660) = \ln I_0(660)/I(660) = \ln(I_0(660)/I(660)e^{-\epsilon_1 c_1 d} e^{-\epsilon_2 c_2 d}) = \epsilon_1 c_1 d + \epsilon_2 c_2 d, \quad (2)$$

$$D(805) = \ln I_0(805)/I(805) = \ln(I_0(805)/I(805)e^{-\epsilon_3 c_1 d} e^{-\epsilon_4 c_2 d}) = \epsilon_3 c_1 d + \epsilon_4 c_2 d, \quad (3)$$

where $\epsilon_1$ and $\epsilon_2$ are the light absorption coefficients of $HbO_2$ and Hb for the red light with wavelength of 660 nm respectively, $\epsilon_3$ and $\epsilon_4$ are the light absorption coefficients of $HbO_2$ and Hb for the infrared light with wavelength of 805 nm respectively and both equal to $\epsilon$ (i.e. $\epsilon_3 = \epsilon_4 = \epsilon$), and d is the thickness of the light-transmitting tissue, the following equations can be reached:

$$C_1 + C_2 = D(805)/\epsilon d,$$

$$C_1 = (D(660) - \epsilon_2 D(805)/\epsilon)/(\epsilon_1 - \epsilon_2)d.$$

By substituting them into the equitation (1), the following equation is reached $$SaO_2 = A \times D(660)/D(805) + B, \quad (4)$$

where $A = \epsilon/(\epsilon_1 - \epsilon_2)$ and $B = \epsilon_2/(\epsilon_1 - \epsilon_2)$.

However, D(660) and D(805) are not only relevant to Hb and $HbO_2$, as expressed in the equations (2) and (3), but also relevant to the absorption of muscles, bones, pigments, adiposes, venous blood and the like in tissues. That is, each of D(660) and D(805) should further include a portion of background absorption as shown in FIG. 3, so the equations (2) and (3) become $$D(660) = \ln I_0(660)/I(660) = \ln(I_0(660)/I_B e^{-\epsilon_1 c_1 \Delta d} e^{-\epsilon_2 c_2 \Delta d}) \quad (5)$$

$$D(805) = \ln I_0(805)/I(805) = \ln(I_0(805)/I_B e^{-\epsilon_3 c_1 \Delta d} e^{-\epsilon_4 c_2 \Delta d}) \quad (6)$$

where $I_0$ is the intensity of incident light, $I_B$ is the intensity of transmitted light when only the background absorption of tissues presents, $\Delta d$ is the variation of the transmission distance as a result of the change from blood-free to blood-perfused. The background absorbance is easily defined as:

$$D_B = \ln(I_0/I_B).$$

Thereby, the following equations can be reached:

$$D(660) - D_B(660) = \epsilon_1 C_1 \Delta d + \epsilon_2 C_2 \Delta d, \quad (7)$$

$$D(805) - D_B(805) = \epsilon_3 C_1 \Delta d + \epsilon_4 C_2 \Delta d, \quad (8)$$

where $\epsilon_3 = \epsilon_4 = \epsilon$, so the equation (4) become $$SaO_2 = A \times (D(660) - D_B(660))/(D(805) - D_B(805)) + B. \quad (9)$$

The equation (9) is the fundamental formula for detecting the blood oxygen saturation.

Generally, the infrared light with one isoabsorption point for wavelength of 805 nm is not utilized to detect the blood oxygen saturation, because it is hard to acquire the precise value of such wavelength and resultantly relatively large error occurs. The infrared light with wavelength of about 940 nm is commonly utilized, for the reason that the variation of the light absorption coefficients of $HbO_2$ and Hb for the wavelength around are more smooth and thus little error usually occurs. When the infrared light with wavelength of 940 nm is utilized, since $\epsilon_3$ is not equal to $\epsilon_4$ (i.e. $\epsilon_3 \neq \epsilon_4$) in the equation (8), the equation (9) becomes the blood oxygen saturation $Spo_2$ $$Spo_2 = (A \times R + B)/(C \times R + D), \quad (10)$$

where $A = \epsilon_1$, $B = -\epsilon_2$, $C = \epsilon_4 - \epsilon_3$, $D = \epsilon_1 - \epsilon_2$, and $$R = \frac{D(660) - D_B(660)}{D(940) - D_B(940)}. \quad (11)$$

It can be known from the above equations that "R" and blood oxygen saturation are one to one correspondence. Since $D = \ln I_0/I = \epsilon cd$, $$R = \frac{\ln I_{R0}/I_{RM} - \ln I_{R0}/I_{Rm}}{\ln I_{I0}/I_{IM} - \ln I_{I0}/I_{Im}} = \frac{\ln I_{Rm}/I_{RM}}{\ln I_{Im}/I_{IM}}, \quad (12)$$

where $I_{RM}$ is the maximum intensity of the transmitted light of red light, $I_{Rm}$ is the minimum intensity of the transmitted light of red light, $I_{R0}$ is the intensity of the incident light of red light, $I_{IM}$ is the maximum intensity of the transmitted light of infrared light, $I_{Im}$ is the minimum intensity of the transmitted light of infrared light, and $I_{I0}$ is the intensity of the incident light of infrared light. With regard to red light, the following equation can be reached:

$$\ln I_{Rm}/I_{RM} = \ln\left(1 - \frac{I_{RM} - I_{Rm}}{I_{RM}}\right). \quad (13)$$

When the ratio of pulsating component to direct current (DC) component, namely $(I_{RM}-I_{Rm})/I_{RM}$ is small, $$\ln\left(1 - \frac{I_{RM} - I_{Rm}}{I_{RM}}\right) \approx \frac{I_{RM} - I_{Rm}}{I_{RM}} \approx \text{pulsating component/DC component.}$$

Accordingly, R can be expressed as follows:

$$R = \frac{Red_{AC}/Red_{DC}}{Ir_{AC}/Ir_{DC}} \quad (14)$$

where $Red_{AC}$ is the alternating current (AC) component of the intensity of transmitted red light (i.e. AC peak value of the intensity of red light), $Red_{DC}$ is the DC component of the intensity of transmitted red light, $Ir_{AC}$ is the AC component of the intensity of transmitted infrared light (i.e. AC peak value of the intensity of the infrared light), and $Ir_{DC}$ is the DC component of the intensity of transmitted infrared light. From the above equations, it can be seen that the main factor influencing the variable R is the AC components of the intensity of transmitted red light and infrared light, because the DC components of the intensity of the two transmitted lights are relatively stable for a period of time after the operating state of the light emitting diode is adjusted and fixed. Now the AC component is calculated by finding out the maximum value and minimum value of the intensity of the two transmitted lights. Therefore, the value of "R" can be calculated if the waveforms of the two transmitted lights in a full pulse wave were known.

In a human body, the arterial blood pulsates in the end parts of tissues as a result of the pulse wave, and the $HbO_2$ and Hb cause the end parts of tissues (such as fingers) to have different transmittivities for red light and infrared light. Nowadays, according to the above principle, the domestic or foreign pulse oximeters operate by irradiating red light and infrared light with a certain intensity to the fingers, detecting the transmitted light intensities of the two lights, and then calculating the blood oxygen saturation based on the ratio of the density variations of the red light and the infrared light after the two lights passing through the fingers and the corresponding equations described above.

According to the principle described above, a device for measuring blood oxygen saturation basically includes a blood oxygen sensor and a signal processing unit The key element of the blood oxygen sensor is a sensor including a light-emitting diode (LED) and a photosensor. The LED can provide the lights of two or more wavelengths. The photosensor can convert the light signals passing through the fingers and containing the information of blood oxygen saturation into electrical signals which are provided to a signal processing module to be digitalized for calculating the blood oxygen saturation.

More particularly, the measuring device can be functionally divided into the following parts, i.e. a power supply circuit, a driving circuit, a signal amplifying and processing part, an A/D (analog/digital) converting circuit, a logical control part, a single-chip microcomputer data processing part and the like. Specifically, as shown in FIG. 1, the measuring device includes: a power supply circuit which outputs two groups of power supply to the whole measuring device, wherein one is +5V for digital circuit and the other one is ±5V for analog circuit, while an AC or DC power supply of ±12V is input; a driving circuit adjusted by the logical control part to output currents with different amplitudes for driving the LED, in order to ensure that a light-receiving device (for example photocell) can output signals with certain amplitudes; a sensor part detecting the light signals passing through the fingers and then converting the light signals into electrical signals which are transmitted to a signal amplifying and processing part; the signal amplifying and processing part which applies differential amplifying process, background photocurrent cancel process, gain adjusting and bias current cancel process to the electrical signals and transmits the electrical signals so-processed to an A/D converting circuit; the A/D converting circuit converting the electrical signals to digital signals which is transmitted to a single-chip microcomputer to be processed; the single-chip microcomputer data processing part whose calculation module simulates and analyzes the waveform based on the sampled signals to find out the maximum value and minimum value of pulse waveform and then calculates the peaks value of the pulse waveform and the blood oxygen saturation; a serial port circuit through which the parameters of pulse wave described above and the blood oxygen saturations isolated by optical coupler are transmitted, wherein the logical control part is utilized to make various parts under the controls of the single-chip microcomputer, such as the control over light-emitting sequential of the sensor, the control over driving current the control over bias current the control over background light cancel, the control of signals A/D converting and the like.

However, there are the following disadvantages in the conventional method described above. The level of perfusion is usually very low for patients. Since it is necessary to measure the AC component of the pulse waveform under this condition, that is, to find out the maximum value and minimum value of the waveform, but the signal to be measured is very poor under low perfusion and the signal-to-noise ratio (SNR) is very low as well, it becomes difficult to find out the waveform. Therefore, errors may occur during the process of measuring the peak value of the pulse wave, and the ratio of AC to DC obtained thus may be wrong, which cause the value of blood oxygen content measured finally to have very low accuracy.

SUMMARY OF THE INVENTION

The present invention intends to provide a method for measuring blood oxygen content, which can accurately measure or monitor the value of blood oxygen content by analyzing and calculating the sampled data of pulse wave, as concerning the case where the level of perfusion is low and signals are poor.

To solve the problem described above, the general concept of the present invention is proposed as follows. Since it can be proved that the integration result of the sampled data of pulse wave corresponds to AC component of the pulse wave, the peak value of waveform, which is necessary to be found in the conventional method, can be replaced by the area integration of signal to calculate the blood oxygen saturation. Thus, only it is necessary to integrate the pulse waveform in a period of time. Further, the disturbance to effective signal by noise can be eliminated with the integration of the noise in the period of time approximating to zero. Therefore, the measuring accuracy of blood oxygen content under low perfusion can be improved.

As the technical solution for realizing the general concept of the present invention, there is provided a method for measuring blood oxygen content under low perfusion, which is used in a device for measuring blood oxygen content, includes the steps of:

a. initializing the device that is applied with power, b. collecting and processing data with a driving circuit of a light emitting device, a bias circuit, a gain circuit and an A/D sampling circuit, which are controlled under a core control module;

c. calculating blood oxygen saturation based on the collected data with a data processing module which integrates the collected data in a period of time with an area integration method; and d. outputting from a communication functional module results of the blood oxygen saturation or pulse rate calculated with the data processing module. fits envelope waveform of a pulse wave In the step of c, the data processing module further fits envelope waveform of the pulse wave and finds out the maximum value and the minimum value of the pulse wave to calculate the blood oxygen saturation with a waveform method based on the collected data. The method, between the steps of c and d, further includes a decision step of deciding the two results acquired from the data processing module with the waveform method and the integration method respectively based on the intensity of the measured signal and generating the final measured result, performed by a decision unit included in the device. The device performs the sampling and measuring by making at least two lights pass through end parts of tissues, wherein one is red light, and the other is infrared light; and in the step of c, the data of the two lights is integrated respectively to calculate the ratio of integration result of the red light to that of the infrared light for replacing the ratio of AC peak value of the intensity of the red light $Red_{AC}$ to that of the infrared light $Ir_{AC}$ received during the period of time.

According to the technical solution described above, the disturbance to effective signal by noise can be eliminated, and the measuring accuracy of blood oxygen content under low perfusion can be improved without increasing the production cost for the measuring device.

DESCRIPTION OF THE PREFERED EMBODIMENTS

Figure 1:
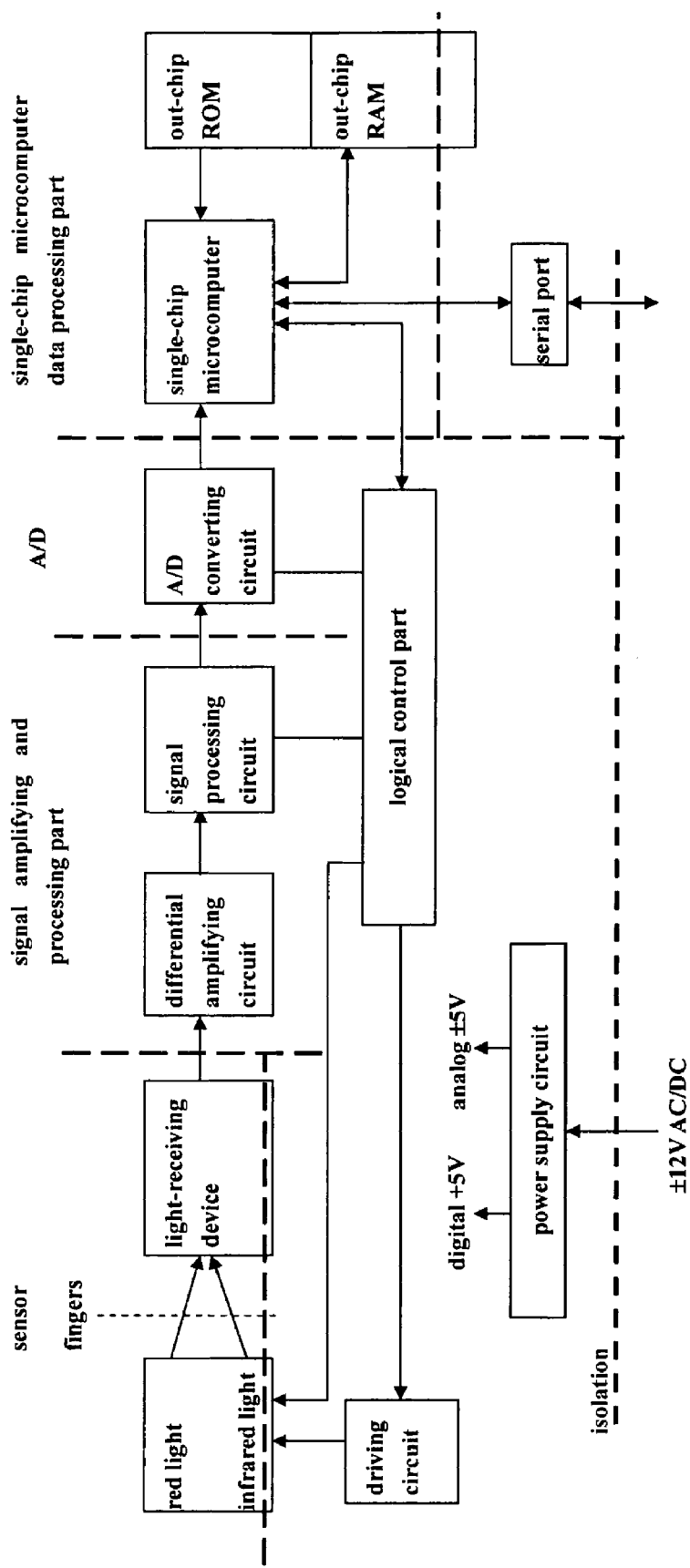
FIG. 1 is a schematic diagram showing the structure of a device for measuring blood oxygen content.
Figure 2:
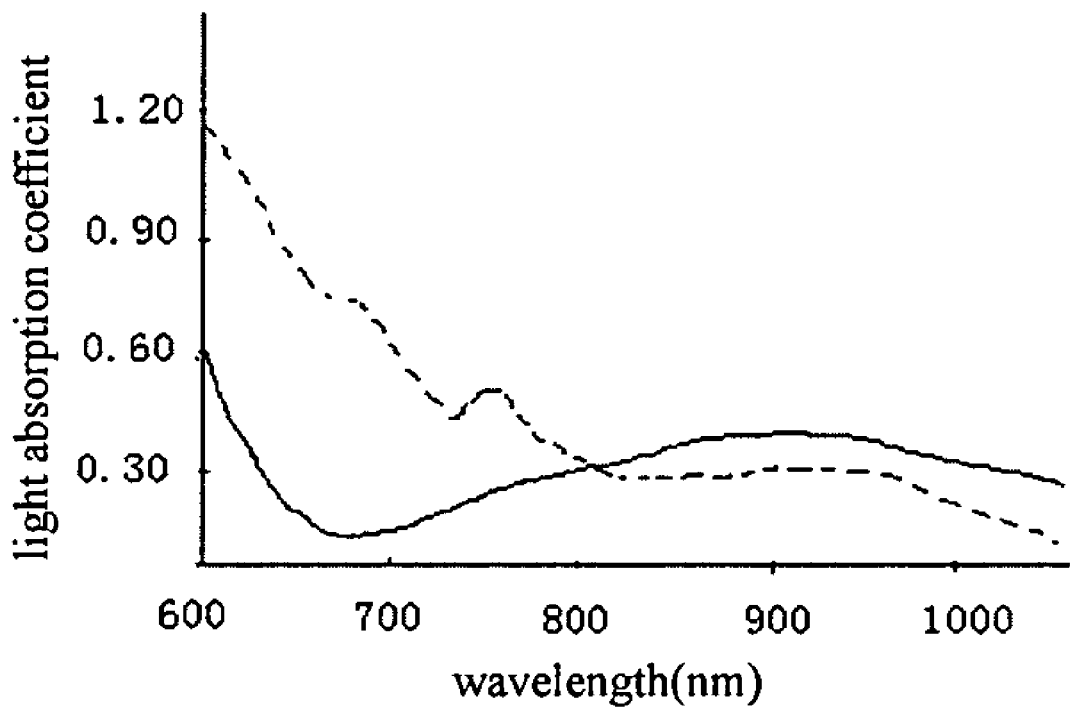
FIG. 2 is a graph showing the curves of light absorption coefficients of $HbO_2$ and Hb with respect to the regions of red light and infrared light.
Figure 3:
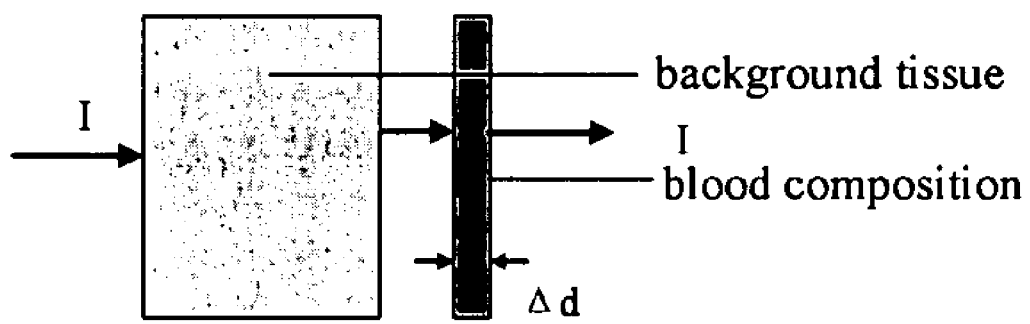
FIG. 3 is a schematic diagram showing the light absorption of the tissue of an animal body.

Now the present invention will be further described in connection with the preferred embodiments shown in the attached figures.

According to the present invention, the disturbance to the signal waveform by noise under low perfusion can be effectively inhibited by adopting an asymptotic integration method. It can be proved theoretically that the asymptotic integration method is equivalent to the conventional method for finding the AC component of waveform under low perfusion. Thus, the asymptotic integration method is used to solve the problem that the measured result of blood oxygen content is inaccurate under low perfusion. At least two Lights are utilized to pass through end parts of tissues for sampling and measuring in the measuring system, wherein one is red light, and the other is infrared light. Firstly, the measured data of the two lights is normalized to acquire the DC ratio of the two lights $$\left(\frac{Ir_{DC}}{Red_{DC}}\right).$$

The normalized waveform of blood oxygen content can be treated as the combination of the waveform under ideal condition with noise. The waveform of blood oxygen content under ideal condition, both red light and infrared light can be treated as the combination of sine waves in different frequency ranges, i.e.

$$Red = a_0 \cos(\omega t) + a_1 \cos(2\omega t) + \ldots + a_{n-1} \cos(n\omega t) + n_{Red} \quad (14)$$

$$Ir = b_0 \cos(\omega t) + b_1 \cos(2\omega t) + \ldots + b_{n-1} \cos(n\omega t) + n_{Ir} \quad (15)$$

where $a_0, a_1, \ldots a_{n-1}$, are the first to nth components of the frequency spectrum of red light respectively, $n_{Red}$ is the noise component in red light, $b_0, b_1, \ldots b_{n-1}$ are the first to nth components of the frequency spectrum of infrared light respectively, $n_{Ir}$ is the noise component in infrared light. The two equations above are integrated respectively to acquire the following ratio:

$$\frac{\int_{t_0}^{t_1} |a_0 \cos(\omega t) + a_1 \cos(2\omega t) + \cdots + a_{n-1} \cos(n\omega t) + n_{Red}| d(\omega t)}{\int_{t_0}^{t_1} |b_0 \cos(\omega t) + b_1 \cos(2\omega t) + \cdots + b_{n-1} \cos(n\omega t) + n_{Ir}| d(\omega t)} = \quad (16)$$

-continued $$\frac{4a_0\sin(\omega t)\big|_0^{\frac{\pi}{2}} + \int_{t_0}^{t_1} |n_{Red}| d(\omega t)}{4b_0\sin(\omega t)\big|_0^{\frac{\pi}{2}} + \int_{t_0}^{t_1} |+n_{Ir}| d(\omega t)}$$

If the noise can be treated as white noise in a period of time, the integration of the noise will be zero. Thereby, the above equation is reduced to $$\frac{4a_0\sin(\omega t)\big|_0^{\frac{\pi}{2}} + \int_{t_0}^{t_1} |n_{Red}| d(\omega t)}{4b_0\sin(\omega t)\big|_0^{\frac{\pi}{2}} + \int_{t_0}^{t_1} |+n_{Ir}| d(\omega t)} = \frac{a_0}{b_0} = \frac{Red_{AC}}{Ir_{AC}}. \quad (17)$$

Therefore, the ratio of AC data of the intensity of the two lights (namely, the AC peak values $Red_{AC}$ and $Ir_{AC}$) received in a period of time can be replaced with the ratio of the integration data of the two lights in the period of time in condition that the integrating time is long enough to make the integration of noises approximate to zero. Furthermore, as the disturbance by noise is eliminated by the method, the measuring under low perfusion will be in well effect.

Figure 5:
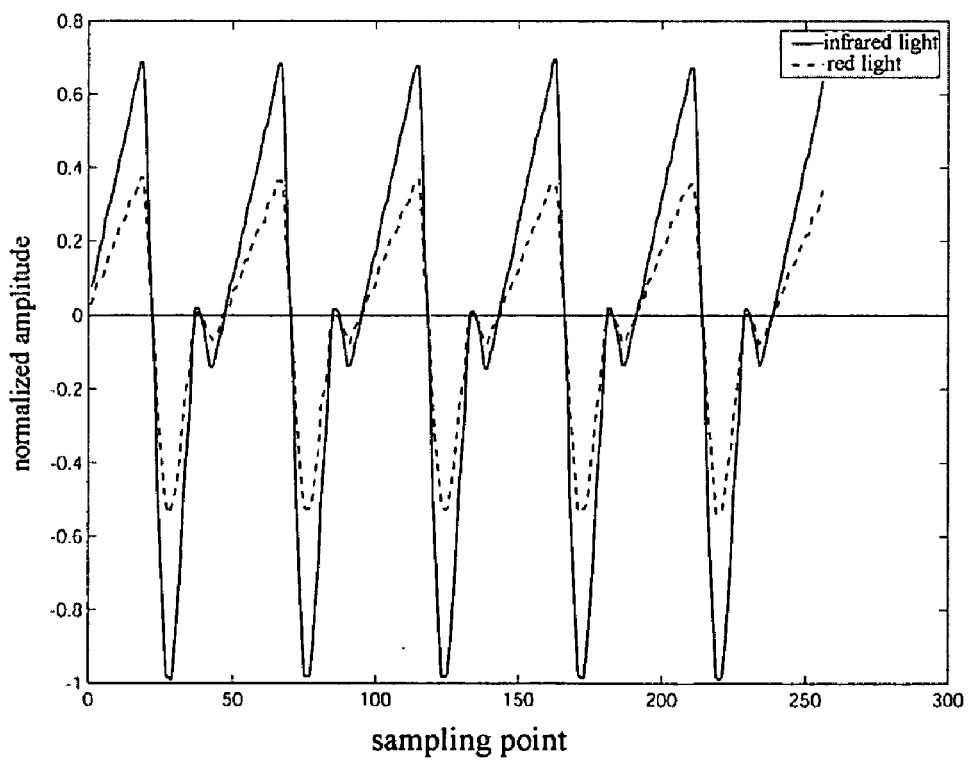
FIG. 5 is a schematic diagram showing waveforms of red light and infrared light simulated from the sampling points.
Figure 6:
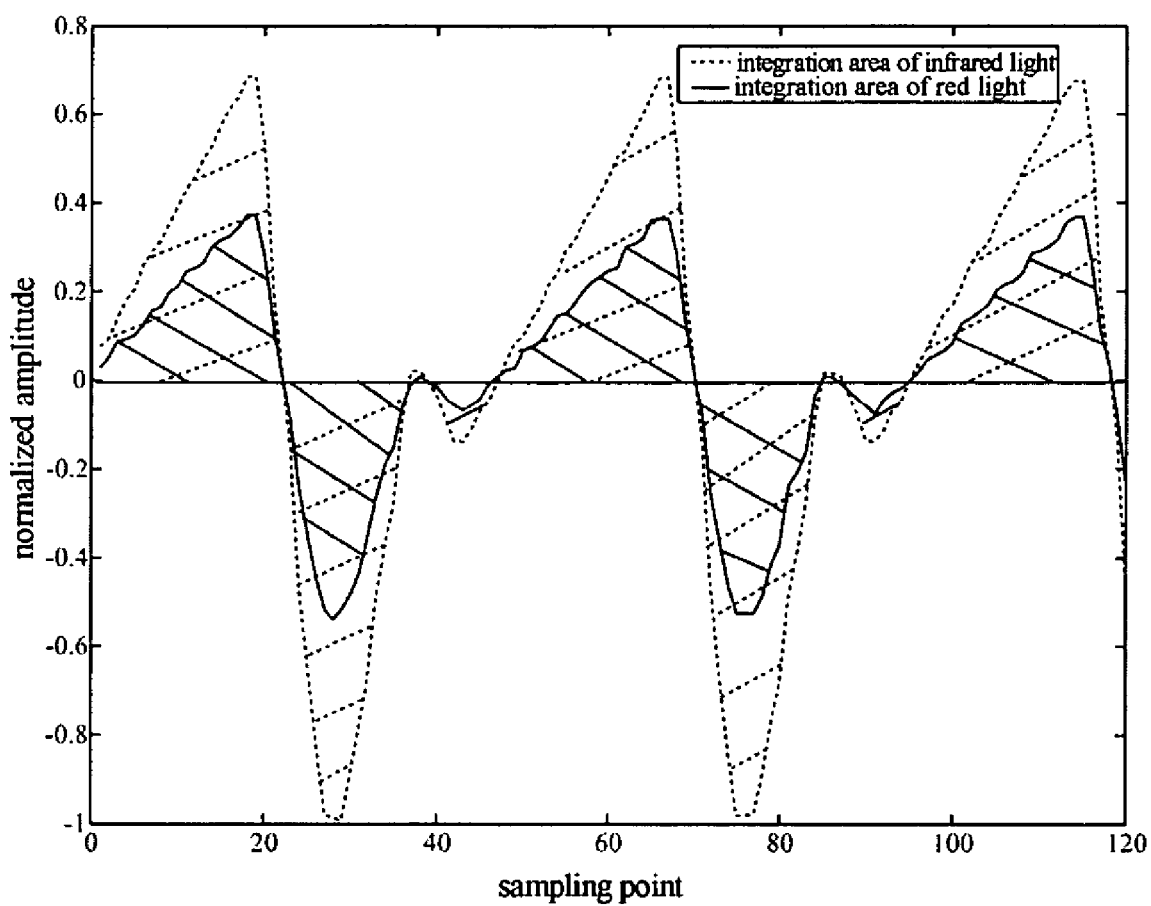
FIG. 6 is a schematic diagram showing results of area integration of red light and infrared light.

The waveforms of red light and infrared light simulated actually from the sampling points are shown in FIG. 5. As shown in FIG. 6, the integrating process is performed by summing the area of the shaded portions surrounded by the curves connecting the sampling points of pulse wave and the time axis, corresponding to red light and infrared light respectively. When the sampling time interval between each of the sampling points is suitable (for example, when sampling at 120 Hz), the area of the portions is approximately equal to the sum of arithmetic product of each sampling amplitudes and the corresponding sampling time interval in a period of time. And the area ratio of the two lights is approximately equal to the AC amplitude (peak value) ratio of the intensity of the two lights in the period of time. Therefore, the blood oxygen saturation can be calculated based on the well-known correlation between R and the blood oxygen saturation by measuring the AC data of the intensity of the two lights. The proper value of the period of time can be selected in the range of 2 to 3 seconds based on experiences.

Figure 7:
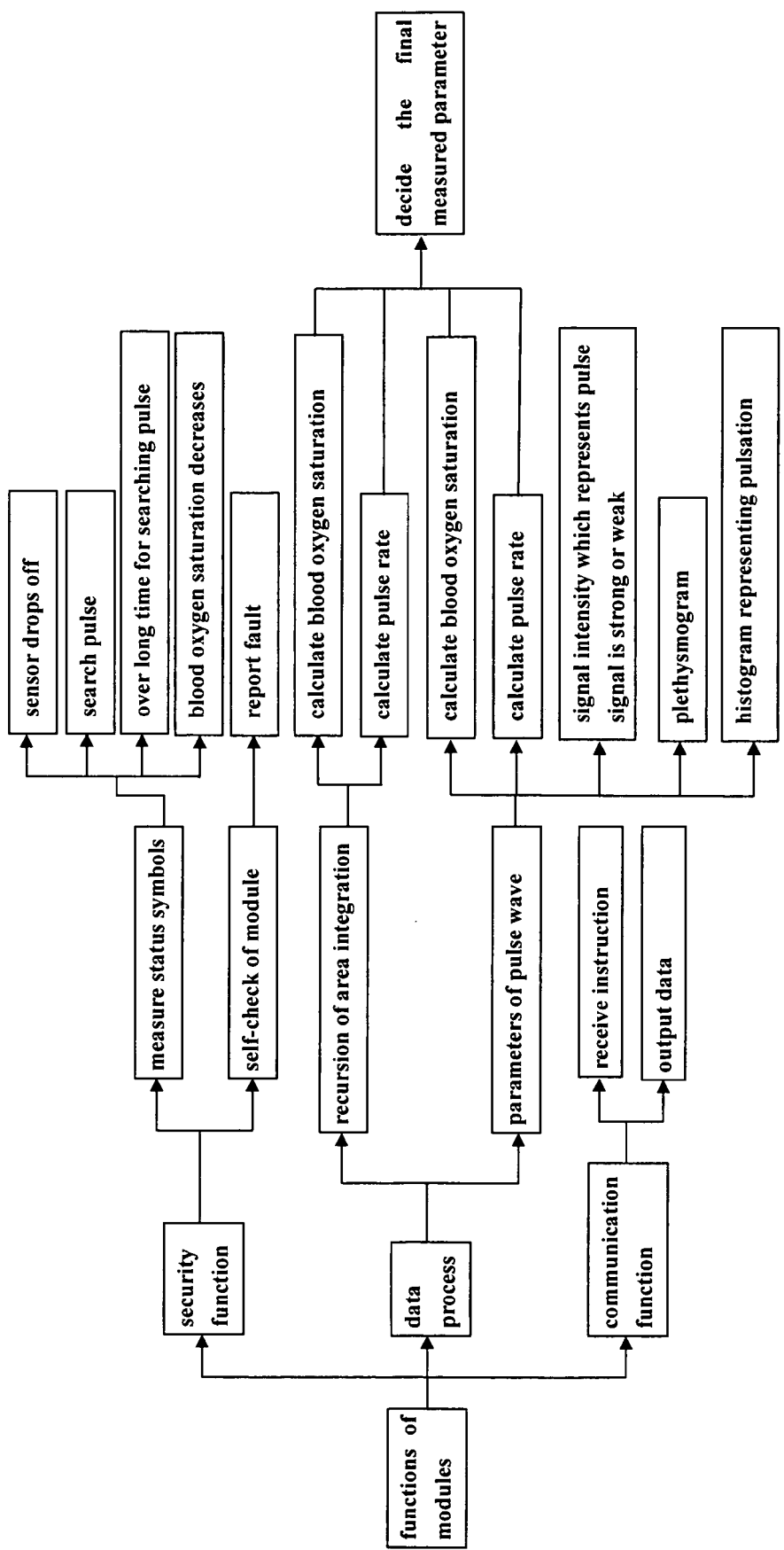
FIG. 7 is a block diagram showing the software modules of the measuring system.

According to the description above, the accuracy of the measuring device under low perfusion can be increased by improving the system software and using the method according to the present invention, based on the measuring device as shown in FIG. 1. FIG. 7 is a block diagram showing the system software module according to the embodiment of the present invention. As shown in FIG. 1, hardware initialization, system self-check of CPU and programs initialization are first performed after the device is applied with power. Thereafter, a core control module starts a security functional module, a data processing module or communication functional module in accordance with the operating status of the system correspondingly, wherein the security functional module measures each of the status symbols of the system or performs system self-check to ensure that the system can operate normally, the data processing module processes the real-time collected data and the calculated result, and the communication functional module makes the system receive instruction or output the data and result. Furthermore, as shown in FIG. 1, the core control module also controls the hardware in different way under each status depending on the measured value during the processes of data collecting and processing, including the control over driving current of light emitting diode, the control over bias circuit and gain, and the control over A/D sampling. In the present embodiment, the process of data processing includes a process of, based on the measured data which is collected in real time and stored in a data buffer, integrating the real-time data in a period of time to calculate the blood oxygen saturation with the recursion process of area integration. Generally, the data processing module also calculates the pulse rate with a zero crossing counter, and the description thereof will be omitted herein. The process of data processing may further include a process of fitting the envelope waveform of the pulse wave and finding out the maximum value and the minimum value of the pulse wave to calculate the blood oxygen saturation with the conventional waveform method, based on the measured data. The system may further include a decision unit. After the steps described above, the method according to the present invention further includes a decision step in which the two results acquired by the data processing module with the waveform method and the integration method respectively are decided and the final measured result is generated based on the intensity of the measured signal.

The precondition for the decision and calculation in the decision step is described as follows. Supposing the result of the blood oxygen saturation acquired with the waveform method is $A_1$, the result of the blood oxygen saturation acquired with the integration method is $A_2$, and the final measured result of the blood oxygen saturation is A, then $$A = a*A_1 + (1-a)*A_2,$$

where the value of "a" can be selected in the range of 1 to 0 depending on the intensity of the measured signal.

The measured signal with relative high intensity, for example, the collected analog signal whose intensity can reach the full range of A/D converting without being amplified, is taken as a reference. If the intensity of actual measured signal is lager than one thirty-second (1/32) of the intensity of the reference, the results of $A_1$ and $A_2$ become approximate to each other, thereby the value of "a" can be selected as 0.5 (i.e. a=0.5), and the average value of $A_1$ and $A_2$ is adopted as the final result; if the intensity of actual measured signal is smaller than one thirty-second (1/32) of the intensity of the reference but larger than one sixty-forth (1/64) of the intensity of the reference, the value of "a" can be selected as 0.4 (i.e. a=0.4); if the intensity of actual measured signal is smaller than one sixty-forth (1/64) of the intensity of the reference but larger than one one-hundred-twenty-eighth (1/128) intensity of the reference, the value of "a" can be selected as 0.3 (i.e. a=0.3); and the like. If the intensity of actual measured signal decreases to a certain degree, the value of "a" can be selected as 0 (i.e. a=0), and the result acquired with the integration method is adopted as the final result.

The precondition of the method described above is that the blood oxygen saturation of the measured object is constant in a period of time. In this case, the longer integrating time results in better measuring effect and then more close to the truth. But once the blood oxygen saturation of the measured object changes (generally changes gently), the overlong integrating time may result in the decrease of measuring sensibility, thereby the real-time measuring or monitoring function of the system is degraded. To solve this problem, during the processes described above, the integration is only performed in a period of time (for example, 2-3 seconds), and a forgetting factor λ is incorporated to retain the real-time monitoring function. Therefore, the ratio of the AC peak value $Red_{AC}$ and $Ir_{AC}$ of the current two lights becomes $$\frac{Red_{AC}}{Ir_{AC}} = \frac{Red_{AC_0} + \lambda Red_{AC_1} + \cdots + \lambda^n Red_{AC_n}}{Ir_{AC_0} + \lambda Ir_{AC_1} + \cdots + \lambda^n Ir_{AC_n}}, \quad (18)$$

where $Red_{AC_0}$, $Ir_{AC_0}$ are the results of the area integration of current time, $Red_{AC_1}$, $Ir_{AC_1}$ are the results of the area integration of last time, and $Red_{AC_n}$, $Ir_{AC_n}$ are the results of the area integration of the former nth time. If the forgetting factor ranges from 0 to 1 (i.e. $0<\lambda<1$), the effect of the data measured more formerly to the calculated result of current time can be ignored after iteration for several times. Therefore, the data, which is calculated more newly for the current time, makes more contribution to the current result. Based on experiences, it is appropriate to select the value of $\lambda$ as 0.8.

Figure 4:
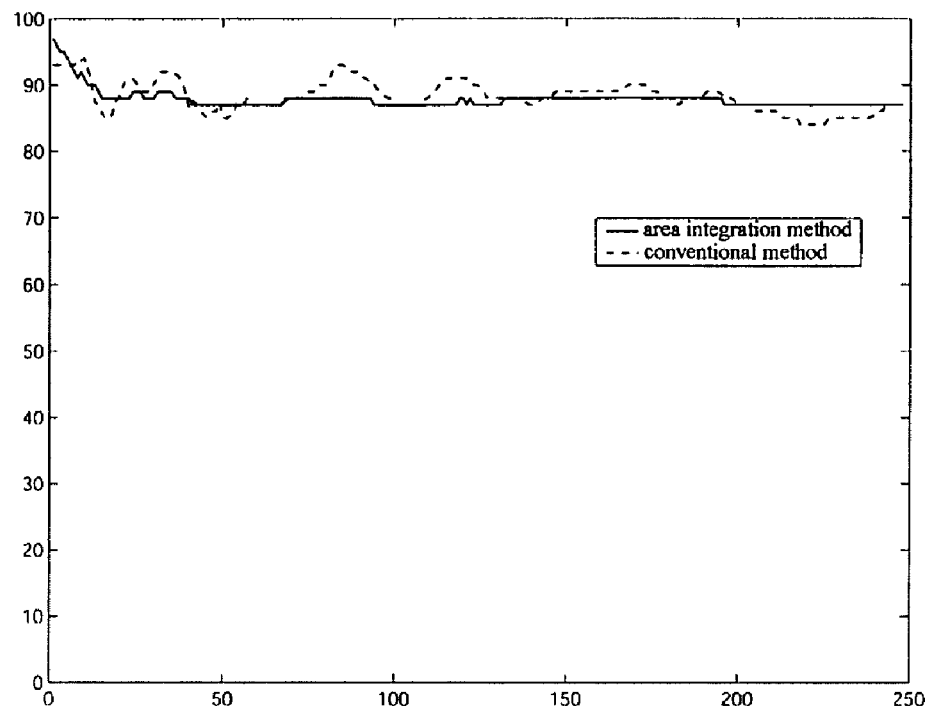
FIG. 4 is a schematic diagram showing the comparison between the results of blood oxygen content measured with the area integration method and conventional method under low perfusion.

FIG. 4 is a schematic diagram showing the comparison between the measured results with the method according to the present invention and the conventional method, wherein the ordinate is blood oxygen saturation in the measuring range of 0 to 100, and the abscissa is time. As seen in FIG. 4, though the undulation of initial measured data is relatively large, the undulation of the measured result with the method according to the present invention is smaller than that of the measured result with the conventional method during normally monitoring. That is to say, the resistance to noise disturbance is getting improved. According to the present invention, it is possible to increase greatly the measuring accuracy of blood oxygen content under low perfusion without increasing the production cost for the measuring device. In particularly, the blood oxygen signal with the intensity of 0.3% can be accurately measured with the conventional method, while the blood oxygen signal with the intensity of 0.1% can be accurately measured with the method according to the present invention.

What is claimed is:

1. A method for measuring blood oxygen content under low perfusion, which is used in a device for measuring blood oxygen content, including the steps of:
   a. initializing the device that is applied with power;
   b. collecting and processing data with a driving circuit of a light emitting device, a bias circuit, a gain circuit and an A/D sampling circuit, which are controlled under a core control module;
   c. calculating blood oxygen saturation based on the collected data with a data processing module which integrates the collected data in a period of time with an area integration method, wherein the collected data is cyclical and the period of time for integration includes more than one cycle; and
   d. outputting from a communication functional module a result of the blood oxygen saturation or pulse rate calculated with the data processing module.

2. The method for measuring blood oxygen content under low perfusion according to claim 1, wherein in the step of c, the data processing module further fits envelope waveform of a pulse wave and finds out the maximum value and minimum value of the pulse wave to calculate the blood oxygen saturation with a waveform method based on the collected data.

3. The method for measuring blood oxygen content under low perfusion according to claim 2, wherein the method, between the steps of c and d, further includes a decision step of deciding between the two results acquired from the data processing module with the waveform method and the integration method respectively based on the intensity of measured signals and generating a final measured result, performed by a decision unit included in the device.

4. The method for measuring blood oxygen content under low perfusion according to claim 3, wherein a precondition for the decision and calculation in the decision step is:

$$A = a*A_1 + (1-a)*A_2,$$

where "$A_1$" is the result of the blood oxygen saturation acquired with the waveform method, "$A_2$" is the result of the blood oxygen saturation acquired with the integration method, "A" is the final measured result of the blood oxygen saturation, and "a" ranges from 1 to 0.

5. The method for measuring blood oxygen content under low perfusion according to claim 2, wherein the device performs the sampling and measuring by making two lights pass through end parts of tissues, wherein one is red light, and the other is infrared light; and in the step of c, the data of the two lights is integrated respectively to calculate the ratio of integration result of the red light to that of the infrared light for replacing the ratio of AC peak value of the intensity of the red light $Red_{AC}$ to that of the infrared light $Ir_{AC}$ received during the period of time.

6. The method for measuring blood oxygen content under low perfusion according to claim 5, wherein:
   in the step of c, the calculation of the data processing module also depends on a forgetting factor $\lambda$ which ranges from 0 to 1, and the ratio of the AC peak value $Red_{AC}$ to $Ir_{AC}$ of the current two lights is $$\frac{Red_{AC}}{Ir_{AC}} = \frac{Red_{AC_0} + \lambda Red_{AC_1} + \cdots + \lambda^n Red_{AC_n}}{Ir_{AC_0} + \lambda Ir_{AC_1} + \cdots + \lambda^n Ir_{AC_n}},$$

where $Red_{AC_0}$, $Ir_{AC_0}$ are the results of the area integration of current time, $Red_{AC_1}$, $Ir_{AC_1}$ are the results of the area integration of last time, and $Red_{AC_n}$, $Ir_{AC_n}$ are the results of the area integration of a former nth time.

7. The method for measuring blood oxygen content under low perfusion according to claim 6, wherein the value of the forgetting factor $\lambda$ is 0.8.

8. The method for measuring blood oxygen content under low perfusion according to claim 3, wherein the device performs the sampling and measuring by making two lights pass through end parts of tissues, wherein one is red light, and the other is infrared light; and in the step of c, the data of the two lights is integrated respectively to calculate the ratio of integration result of the red light to that of the infrared light for replacing the ratio of AC peak value of the intensity of the red light $Red_{AC}$ to that of the infrared light $Ir_{AC}$ received during the period of time.

9. The method for measuring blood oxygen content under low perfusion according to claim 8, wherein:
   in the step of c, the calculation of the data processing module also depends on a forgetting factor $\lambda$ which ranges from 0 to 1, and the ratio of the AC peak value $Red_{AC}$ to $Ir_{AC}$ of the current two lights is $$\frac{Red_{AC}}{Ir_{AC}} = \frac{Red_{AC_0} + \lambda Red_{AC_1} + \cdots + \lambda^n Red_{AC_n}}{Ir_{AC_0} + \lambda Ir_{AC_1} + \cdots + \lambda^n Ir_{AC_n}},$$

where $Red_{AC_0}$, $Ir_{AC_0}$ are the results of the area integration of current time, $Red_{AC_1}$, $Ir_{AC_1}$ are the results of the area integration of last time, and $Red_{AC_n}$, $Ir_{AC_n}$ are the results of the area integration of a former nth time.

10. The method for measuring blood oxygen content under low perfusion according to claim 9, wherein the value of the forgetting factor λ is 0.8.

11. The method for measuring blood oxygen content under low perfusion according to claim 4, wherein the device performs the sampling and measuring by making two lights pass through end parts of tissues, wherein one is red light, and the other is infrared light; and in the step of c, the data of the two lights is integrated respectively to calculate the ratio of integration result of the red light to that of the infrared light for replacing the ratio of AC peak value of the intensity of the red light $Red_{AC}$ to that of the infrared light $Ir_{AC}$ received during the period of time.

12. The method for measuring blood oxygen content under low perfusion according to claim 11, wherein:
in the step of c, the calculation of the data processing module also depends on a forgetting factor λ which ranges from 0 to 1, and the ratio of the AC peak value $Red_{AC}$ to $Ir_{AC}$ of the current two lights is $$\frac{Red_{AC}}{Ir_{AC}} = \frac{Red_{AC_0} + \lambda Red_{AC_1} + \cdots + \lambda^n Red_{AC_n}}{Ir_{AC_0} + \lambda Ir_{AC_1} + \cdots + \lambda^n Ir_{AC_n}},$$

where $Red_{AC_0}$, $Ir_{AC_0}$ are the results of the area integration of current time, $Red_{AC_1}$, $Ir_{AC_1}$ are the results of the area integration of last time, and $Red_{AC_n}$, $Ir_{AC_n}$ are the results of the area integration of a former nth time.

13. The method for measuring blood oxygen content under low perfusion according to claim 12, wherein the value of the forgetting factor λ is 0.8.

14. The method for measuring blood oxygen content under low perfusion according to claim 1, wherein the device performs the sampling and measuring by making two lights pass through end parts of tissues, wherein one is red light, and the other is infrared light; and in the step of c, the data of the two lights is integrated respectively to calculate the ratio of integration result of the red light to that of the infrared light for replacing the ratio of AC peak value of the intensity of the red light $Red_{AC}$ to that of the infrared light $Ir_{AC}$ received during the period of time.

15. The method for measuring blood oxygen content under low perfusion according to claim 14, wherein:
in the step of c, the calculation of the data processing module also depends on a forgetting factor λ which ranges from 0 to 1, and the ratio of the AC peak value $Red_{AC}$ to $Ir_{AC}$ of the current two lights is $$\frac{Red_{AC}}{Ir_{AC}} = \frac{Red_{AC_0} + \lambda Red_{AC_1} + \cdots + \lambda^n Red_{AC_n}}{Ir_{AC_0} + \lambda Ir_{AC_1} + \cdots + \lambda^n Ir_{AC_n}},$$

where $Red_{AC_0}$, $Ir_{AC_0}$ are the results of the area integration of current time, $Red_{AC_1}$, $Ir_{AC_1}$ are the results of the area integration of last time, and $Red_{AC_n}$, $Ir_{AC_n}$ are the results of the area integration of a former nth time.

16. The method for measuring blood oxygen content under low perfusion according to claim 15, wherein the value of the forgetting factor λ is 0.8.

17. The method for measuring blood oxygen content under low perfusion according to claim 1, wherein in the step of c, the period of time for integration is 2-3 seconds.

18. The method for measuring blood oxygen content under low perfusion according to claim 1, wherein the integration determines an area between the collected data and a normalized value of the collected data.

* * * * *